United States Patent
Steinbacher

(10) Patent No.: US 11,162,896 B2
(45) Date of Patent: Nov. 2, 2021

(54) METHOD AND GAS ANALYZER FOR MEASURING THE CONCENTRATION OF A GAS COMPONENT IN A MEASUREMENT GAS

(71) Applicant: Siemens Aktiengesellschaft, Munich (DE)

(72) Inventor: Franz Steinbacher, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 17/035,933

(22) Filed: Sep. 29, 2020

(65) Prior Publication Data

US 2021/0096068 A1 Apr. 1, 2021

(30) Foreign Application Priority Data

Sep. 30, 2019 (EP) .................................... 19200607

(51) Int. Cl.
*G01N 21/00* (2006.01)
*G01N 21/39* (2006.01)
*G01N 33/00* (2006.01)

(52) U.S. Cl.
CPC ......... *G01N 21/39* (2013.01); *G01N 33/0027* (2013.01); *G01N 2021/399* (2013.01); *G01N 2201/0612* (2013.01); *G01N 2201/12* (2013.01)

(58) Field of Classification Search
CPC .. G01N 21/39; G01N 21/3504; G01N 21/031; G01N 2021/399; G01J 3/42

(Continued)

(56) References Cited

U.S. PATENT DOCUMENTS 6,064,488 A 5/2000 Brand et al.
6,341,521 B1 1/2002 Bartolomey et al.
(Continued)

FOREIGN PATENT DOCUMENTS

DE 102015207192 10/2016
EP 3001180 3/2016
(Continued)

OTHER PUBLICATIONS

Jingjing Wang et al: "High-sensitivity-off-axis integrated cavity output spectroscopy implementing wavelength modulation and white noise perturbation"; Optic Letters; vol. 44; No. 13; Jul. 1, 2019; p. 3298; Abstract; p. 3298, right column, Par. 3-p. 3300, right column, Abs. 1; Fig. 1.
(Continued)

*Primary Examiner* — Md M Rahman
(74) *Attorney, Agent, or Firm* — Cozen O'Connor

(57) ABSTRACT

Method and gas analyzer for measuring the concentration of a gas component in a measurement gas, a wavelength-tunable laser diode is actuated with a current, one part of the light generated by the laser diode is guided through the measurement gas to a measuring detector to generate a measuring signal, the other part of the light is guided to a monitor detector to generate a monitor signal, the current is varied in periodically consecutive scanning intervals to scan an absorption line of interest of the gas component as a function of the wavelength, the current is further modulated with a radio-frequency noise signal having a lower cut-off frequency selected as a function of the properties of the laser diode and high enough to ensure no wavelength modulation occurs and the measuring signal is correlated with the monitor signal and then evaluated to generate a measurement result.

16 Claims, 2 Drawing Sheets

(58) Field of Classification Search
USPC .......................................................... 356/437
See application file for complete search history.

(56) References Cited

U.S. PATENT DOCUMENTS

| | | |
|---|---|---|
| 2005/0046852 A1 | 3/2005 | Larking et al. |
| 2014/0361172 A1 | 12/2014 | Little, III et al. |
| 2015/0177131 A1* | 6/2015 | Liu .................... G01N 21/3554 356/326 |
| 2016/0299065 A1 | 10/2016 | Steinbacher |
| 2017/0045446 A1* | 2/2017 | Beyer ..................... G01J 3/433 |
| 2018/0356266 A1* | 12/2018 | Robbins ................. G01N 21/39 |
| 2020/0088576 A1 | 3/2020 | Depenheuer |

FOREIGN PATENT DOCUMENTS

| | | |
|---|---|---|
| EP | 3339839 | 6/2018 |
| WO | 2016050577 | 4/2016 |

OTHER PUBLICATIONS

EP Search Report dated Apr. 28, 2020 based on EP 19200607 filed Sep. 30, 2019.
Office Action dated Aug. 11, 2021 issued in European Patent Application No. 19200607.0.

* cited by examiner

METHOD AND GAS ANALYZER FOR MEASURING THE CONCENTRATION OF A GAS COMPONENT IN A MEASUREMENT GAS

BACKGROUND OF THE INVENTION

1. Field of the Invention

The invention relates to a method for measuring the concentration of a gas component in a measurement gas and to a gas analyzer for measuring the concentration of the gas component in the measurement gas.

2. Description of the Related Art

Laser spectrometers are particularly used for optical gas analysis in process measuring engineering. Herein, a laser diode generates light in the infrared range, which is guided along a measuring length in a process plant or a gas cell through a process gas (measurement gas) and then detected. The wavelength of the light is tuned to a specific absorption line of the gas component to be measured in each case, where the laser diode scans the absorption line periodically as a function of the wavelength. For this, the laser diode is actuated with a ramp-shaped current signal or triangular current signal within consecutive scanning intervals. With direct absorption spectroscopy (DAS), the concentration of the gas component of interest can be determined directly from the reduction in light intensity (absorption) detected at the location of the absorption line. With wavelength modulation spectroscopy (WMS), during the comparatively slow wavelength-dependent scanning of the absorption line, the wavelength of the generated light is additionally sinusoidally modulated with a frequency in the kHz range and low amplitude. The absorption line does not have a linear profile. As a result, higher order harmonics are also generated in the detector or measuring signal. Usually, the measuring signal is demodulated at an nth harmonic, preferably the second harmonic, via a phase-sensitive lock-in technique and evaluated for each scan interval to produce a measurement result containing the concentration of the gas component to be measured.

The detection and determination limit for the measurement of the concentration of the gas component is limited by noise superimposed on the measuring signal. The noise is primarily composed of the noise from the gas analyzer on the laser and detector side and noise from the measuring length (caused by turbulence, particles).

WO 2016/050577 A1 or DE 10 2015 207 192 A1 discloses additional modulation of the current for actuating the laser diode additionally with a radio frequency (RF) selected as a function of the properties of the laser diode high enough to ensure that no wavelength modulation of the generated light occurs. The detector or measuring signal is demodulated at the frequency of the additional RF modulation and the demodulated measuring signal obtained hereby evaluated to generate the measurement result.

The wavelength of the light is set or changed via the internal temperature of the laser diode and this internal temperature can in turn be set or changed via the power loss due to the laser current and via the ambient temperature. As a result, wavelength modulation can only be performed at low modulation frequencies, maximum in the kHz range. On the other hand, at higher frequencies in the MHz range, only the intensity of the light but not its wavelength is modulated. RF modulation copies the baseband of the measuring signal to be evaluated from the frequency range disrupted by the noise of the gas analyzer and the measuring length close to DC into a radio radio-frequency range in which this noise is no longer present.

RF modulation can only be performed up to the modulation depth limit of the laser diode. Consequently, DE 10 2015 207 192 A1 describes multiplying the RF modulation with a spreading code such that the signal energy of the RF modulation is distributed over a broad frequency spectrum and therefore a higher total energy that can be evaluated is available. On the detector side, the demodulated measuring signal is correlated by correlation with the spreading code and the correlation signal obtained is evaluated. The correlation of the demodulated measuring signal with the spreading code also reduces the gas analyzer noise in the measuring signal because the noise does not correlate with the spreading code.

Jingjing Wang et al: "High-sensitivity off-axis integrated cavity output spectroscopy implementing wavelength modulation and white noise perturbation", Optics Letters, Vol. 44, No. 13, Jul. 1, 2019, page 3298, discloses an off-axis integrated cavity output spectrometer (OA-ICOS), with which a gas cell containing the measurement gas is formed as an optical resonator into which the laser beam is coupled offset and tilted to the optical axis and, therefore, excites a plurality of resonator modes. The current of the laser diode, which is modulated in a ramp-shaped manner for wavelength scanning and sinusoidally for wavelength modulation, is additionally modulated with white noise to suppress the noise caused by fluctuations of the resonator modes (residual cavity-mode fluctuation). However, the coupling-in of the white noise also leads to a broadening of the absorption lines and a reduction in their height such that it is necessary to find a compromise between efficient suppression of the resonator-mode noise and the lowest possible deformation of the spectral line shape.

US 2005/046852 A1 discloses a WMS laser spectrometer with a beam splitter, which guides one part of the light generated by the laser diode through the measurement gas to a measuring detector, and guide the other part to a monitor detector. The current source that generates the current for the laser diode is actuated at regular intervals outside the scanning periods for the wavelength-dependent scanning of the absorption line of interest with a burst signal. This burst is detected in both the measuring signal and the monitor signal and used to normalize the measurement.

EP 3 339 839 A1 discloses a WMS laser spectrometer with a beam splitter, which guides one part of the light generated by the laser diode through the measurement gas, and guides the other part through a reference gas to a reference detector, which detects the absorption spectrum of the reference gas. To ascertain the concentration of the gas component of interest of the measurement gas, the separately detected absorption spectrum of the reference gas is subtracted from that of the measurement gas.

SUMMARY OF THE INVENTION

It is an object of the invention is based to provide a gas analyzer and method that improve a measuring signal-noise ratio.

This and other objects and advantages are achieved in accordance with the invention by a gas analyzer and method in which, for measuring the concentration of a gas component in a measurement gas via a gas analyzer, a wavelength-tunable laser diode is actuated with a current, one part of the light generated by the laser diode is guided through the measurement gas to a measuring detector to generate a measuring signal, another part of the light is guided to a monitor detector to generate a monitor signal, the current is varied in periodically consecutive scanning intervals to scan an absorption line of interest of the gas component as a function of the wavelength, the current is further modulated with a radio-frequency noise signal having a lower cut-off frequency that selected as a function of properties of the laser diode at a level high enough to ensure that no wavelength modulation occurs and the measuring signal is correlated with the monitor signal and then evaluated to generate a measurement result.

In contrast to the conventional method described in DE 10 2015 207 192 A1, in accordance with the invention the current for the laser diode is modulated directly with radio-frequency noise without an RF carrier. The measuring signal obtained from the light of the laser diode after the measurement gas has passed through is correlated with the monitor signal generated from the light of the laser diode. As a result, the noise of the components, such as the laser diode and/or the driver electronics, on the laser side of the gas analyzer becomes part of the modulation with the radio-frequency noise signal such that the noise of the measurement signal only differs from the noise of the monitor signal in the influences caused by absorption in the measurement gas.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For a further explanation of the invention, reference is made below to the drawing figures, in which.

DETAILED DESCRIPTION OF THE EXEMPLARY EMBODIMENTS

Figure 1:
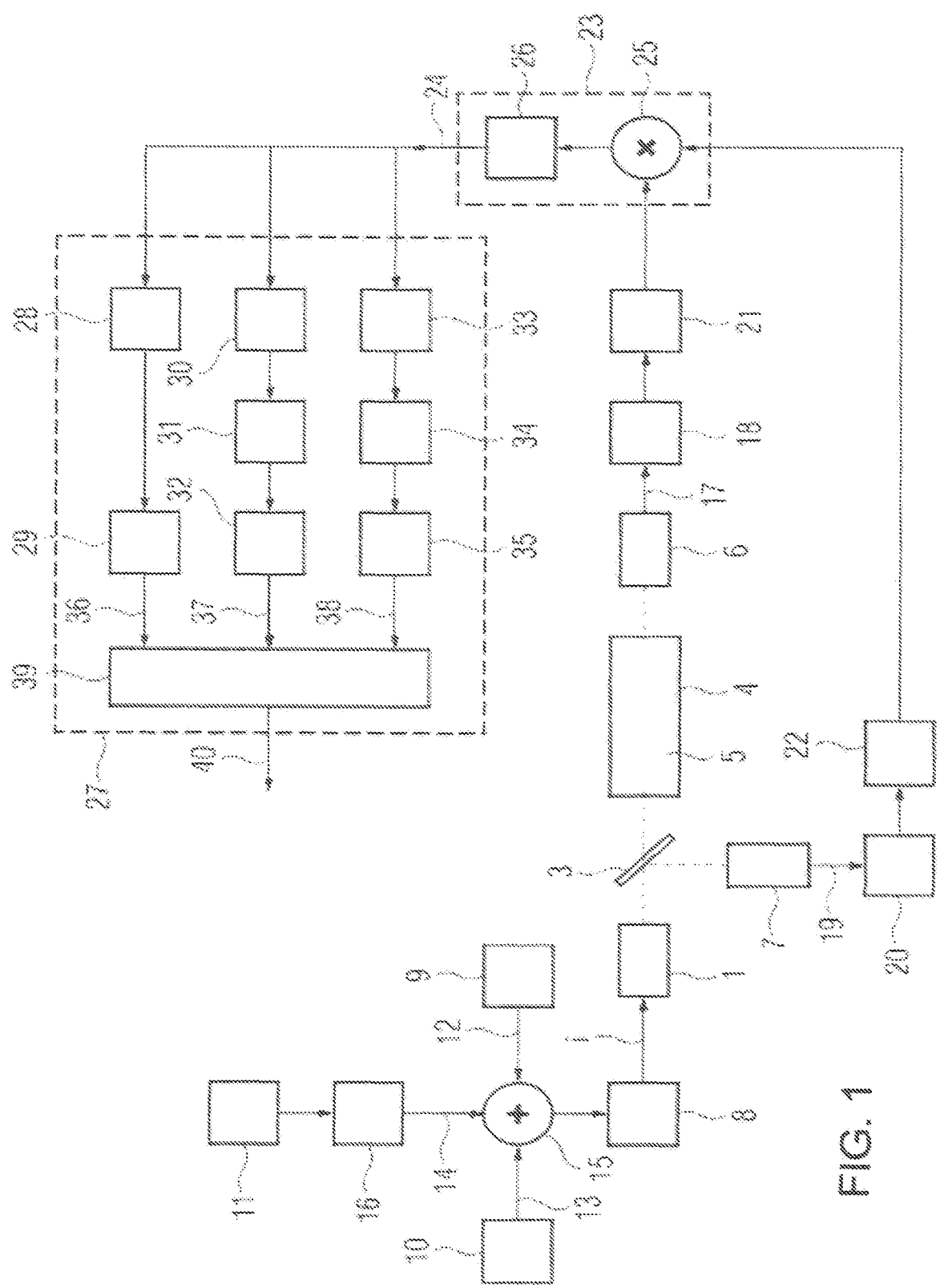
FIG. 1 shows a greatly simplified exemplary block diagram of a gas analyzer in accordance with the invention.

With reference to FIG. 1, the gas analyzer contains a laser diode 1, one part of the light 2 of which is guided via a beam splitter 3 through a measurement gas 5 contained in a measurement volume 4, such as a gas cell or a process gas line, to a measuring detector 6 and the other part of the light of which is guided to a monitor detector 7. The laser diode 1 is actuated by a controllable current source (driver) 8 with an injection current i, where the intensity and the wavelength of the generated light 2 are dependent upon the current i and the operating temperature of the laser diode 1. In order to vary and modulate the current i, a signal generator 9, an optional low-frequency (LF) modulation device 10 and a noise-signal generator 11 generate different signals 12, 13, 14, which are supplied to the current source 8 via a summator 15.

The signal 12 of the signal generator 9 varies the current i periodically in accordance with a prespecified, preferably ramp-shaped or triangular function to scan at least one selected absorption line of a gas component of interest in the measurement gas 5 with the more or less linear wavelength of the generated light 2 as a function of the wavelength. The signal 12 can additionally contain bursts, which follow one another at regular intervals, such as after each scanning period, and during which the laser diode 1 is switched on and off with a burst frequency of, such as 3 kHz, in order to enable the measurement to be normalized at a subsequent point in time.

The low-frequency (LF) modulation device 10 is provided when the concentration of the gas component of interest is to be determined based on wavelength modulation spectroscopy (WMS). Here, the current i, and hence the wavelength of the generated light 2, is modulated sinusoidally with a frequency f in the kHz range (for example <100 kHz) and low amplitude.

The signal 14 generated by the noise-signal generator 11 and supplied to the controllable current source 8 is a radio-frequency noise signal having a lower cut-off frequency that is selected as a function of the properties of the laser diode 1, for example, 5 MHz to 100 MHz, high enough or here, for example, determined by a high-pass filter 16 to ensure that no wavelength modulation occurs and only the intensity of the generated light 2 is modulated.

The measuring detector 6 generates a measuring signal 17 as a function of the detected light intensity and the measuring signal is amplified and digitized in a measuring signal processing stage 18. Similarly, the monitor detector 7 generates a monitor signal 19, which is amplified and digitized in a monitor signal processing stage 20. The digitized measuring signal 17 and the digitized monitor signal 19 are each high-pass filtered in filters 21 or 22, here with the lower cut-off frequency of the noise signal 14, for example, before they are supplied to a correlator 23, which correlates the measuring signal 17 with the monitor signal 19 and generates a correlation signal 24. The high-pass filtering causes the signal components of the ramp-shaped or triangular modulation and LF modulation to be withheld from the correlator 23 such that the correlation of the measuring signal 17 with the monitor signal 19 only occurs with respect to the noise contained therein. In the depicted exemplary embodiment, the two signal processing paths for the measuring signal 17 and the monitor signal 19 are identical or contain structurally identical electronics such that the delays of the two signals 17, 19 are the same and the correlator 23 can be configured in a simple manner in the form of a multiplier 25 with a downstream low pass (averaging unit, integrator) 26. The correlation peak always occurs when the correlated signals are congruent and the noise changes constantly. As a consequence, the two signals 17, 19 must not be temporally offset from one another. If, therefore, for example in the case of an in-situ-gas analyzer with measuring heads mounted on opposite sides of a flue gas duct, the monitor detector 19 is arranged together with the laser diode 1 in one measuring head and the measuring detector 17 in the other measuring head, then runtime delays due to signal paths of different lengths between the detectors 6, 7 and the correlator 23 must be compensated by buffers.

The correlation signal 24 is subsequently evaluated in an evaluation device 27 based on direct absorption spectroscopy (DAS) and/or wavelength modulation spectroscopy (WMS).

For DAS evaluation, the correlation signal 24 passes through a low-pass filter 28 before being evaluated and normalized in a computing facility 29. The cut-off frequency of the low pass filter 28 is selected such that it is higher than the frequency with which the intensity of the light 2 varies during the wavelength-dependent scanning of the selected absorption line of the gas component of interest in the measurement gas 5 achieved via the ramp-shaped or triangular signal 12. In the example depicted here, the cut-off frequency of the low pass filter 28 is, for example. 3 kHz.

For WMS evaluation at the single LF modulation frequency f, after passing through a bandpass filter 30 with the center frequency f, the correlation signal 24 is detected phase-sensitively in a lock-in detector 31 at the frequency 2f and then in evaluated in a computing facility 32.

For WMS evaluation at the double (or n-fold) LF modulation frequency f, after passing through a bandpass filter 33 with the center frequency 2f (or nf), the correlation signal 24 is detected phase-sensitively in a lock-in detector 34 at the frequency 2f (or nf) and then evaluated in a computing facility 35. In the example depicted here, the bandwidth of the bandpass filter 30, 33 is, for example, 3 kHz.

The results 36, 37, 38 of the DAS and WMS evaluations are combined in a further computing device 39 in order to finally obtain the concentration of the gas component to be measured as a measuring result 40.

Figure 2:
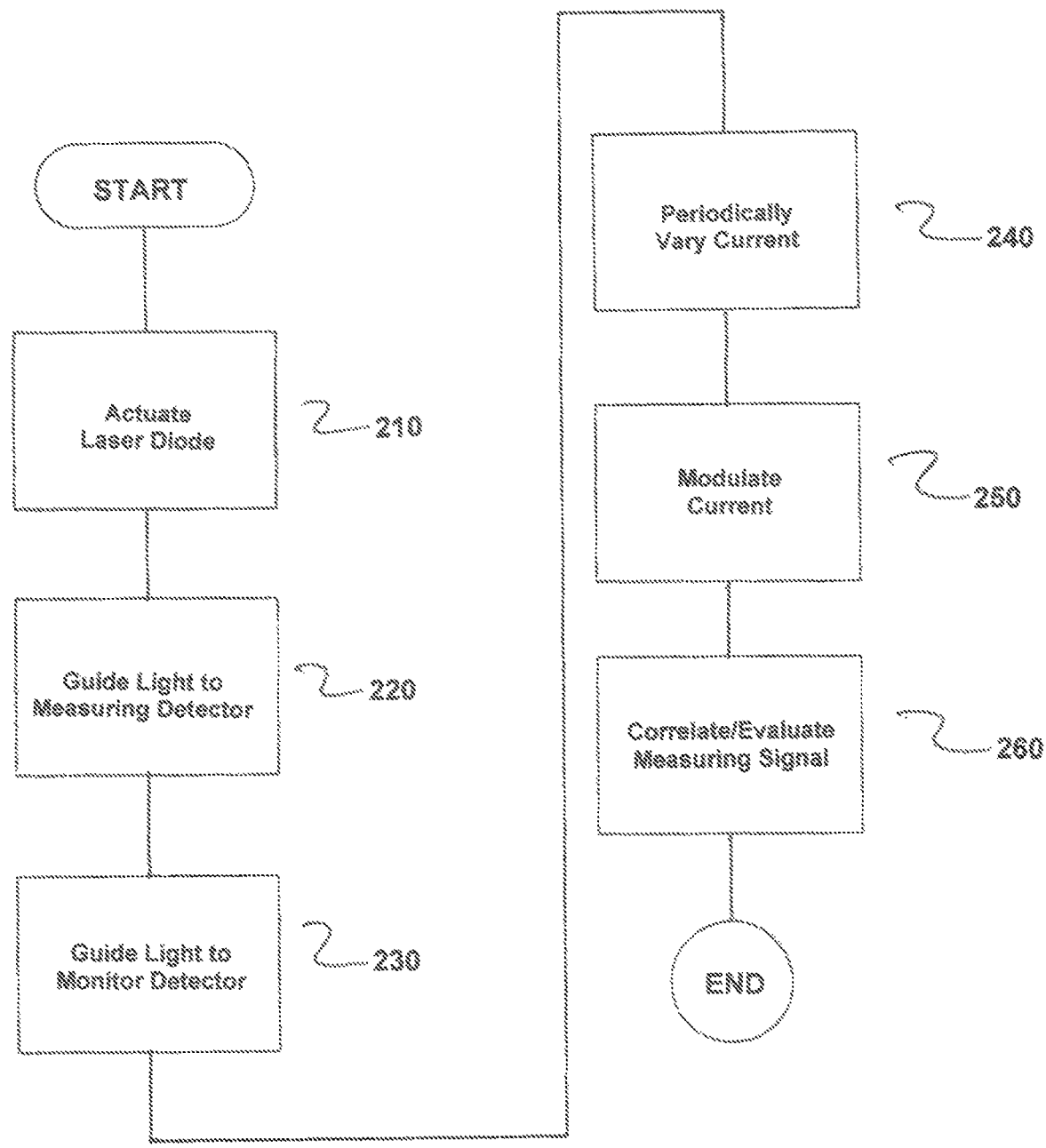
FIG. 2 is a flowchart of the method in accordance with the invention.

FIG. 2 is a flowchart of the method for measuring the concentration of a gas component in a measurement gas 5 via a gas analyzer. The method comprises actuating a wavelength tunable laser diode 1 with a current i, as indicated in step 210.

Next, one part of light 2 generated by the laser diode 1 is through the measurement gas 5 to a measuring detector 6 to generate a measuring signal 17, as indicated in step 220. Next, another part of the generated light 2 is guided to a monitor detector 7 to generate a monitor signal 19, as indicated in step 230.

Next, the current i is varied in periodically consecutive scanning intervals to scan an absorption line of interest of a gas component as a function of a wavelength, as indicated in step 240. The current i is modulated with a radio-frequency noise signal 14, as indicated in step 250. Here, the lower cut-off frequency of the radio-frequency noise signal 14 is selected as a function of properties of the laser diode 1 at a level that ensure no wavelength modulation occurs.

Next, the measuring signal 17 is correlated with the monitor signal 19 and the correlated measuring signal 17 is evaluated to generate a measurement result 40, as indicated in step 260.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for measuring the concentration of a gas component in a measurement gas via a gas analyzer, the method comprising:

actuating a wavelength-tunable laser diode with a current;
guiding one part of light generated by the laser diode through the measurement gas to a measuring detector to generate a measuring signal;
guiding another part of the generated light to a monitor detector to generate a monitor signal;
varying the current in periodically consecutive scanning intervals to scan an absorption line of interest of a gas component as a function of a wavelength;
modulating the current with a radio-frequency noise signal, a lower cut-off frequency of the radio-frequency noise signal being selected as a function of properties of the laser diode a level which ensure no wavelength modulation occurs; and
correlating the measuring signal with the monitor signal and evaluating the correlated measuring signal to generate a measurement result.

2. The method as claimed in claim 1, wherein the measuring signal and, before the correlation, the monitor signal is high-pass filtered with a cut-off frequency lower than a frequency of the radio-frequency noise signal.

3. The method as claimed in claim 2, wherein the measurement is performed based on direct absorption spectroscopy.

4. The method as claimed in claim 1, wherein measurement is performed based on direct absorption spectroscopy.

5. The method as claimed in claim 1, wherein the measurement is based on wavelength modulation spectroscopy; wherein the current of the laser diode is additionally modulated with a lower amplitude and at least one additional frequency selected at a level which ensures wavelength modulation occurs.

6. A gas analyzer for measuring the concentration of a gas component in a measurement gas, comprising:

a wavelength-tunable laser diode;
a current source which supplies current to the wavelength-tunable laser diode;
a signal generator which controls the current source to vary the current to perform wavelength-dependent scanning of an absorption line of interest of the gas component in periodically consecutive scanning intervals;
a noise-signal generator which controls the current source to modulate the current with a radio-frequency noise signal having a lower cut-off frequency which is selected as a function of properties of the laser diode a level which ensure no wavelength modulation occurs;
a measuring detector which generates a measuring signal;
a monitor detector which generates a monitor signal;
a beam splitter which guides one part of the light generated by the laser diode through the measurement gas to the measuring detector and guide another part to the monitor detector;
a correlator which correlates the measuring signal with the monitor signal and generates a correlation signal; and
an evaluation device which evaluates the generated correlation signal to generate a measurement result.

7. The gas analyzer as claimed in claim 6, wherein the correlator comprises a multiplier with a downstream low pass/averaging unit/integrator.

8. The gas analyzer as claimed in claim 7, further comprising:

high-pass filters arranged upstream of the correlator, said high-pass filters high-pass filtering the measuring signal and the monitor signal before correlation with a cut-off frequency having a level which is lower than a frequency level of the radio-frequency noise signal.

9. The gas analyzer as claimed in claim 7, wherein the evaluation device is configured to evaluate the correlation signal based on direct absorption spectroscopy.

10. The gas analyzer as claimed in claim 7, further comprising:
a low-frequency modulation device which controls the current source to additionally modulate the current with a lower amplitude and at least one additional frequency which is selected at a level which ensure wavelength modulation occurs;
wherein the evaluation device is configured to evaluate the correlation signal based on wavelength modulation spectroscopy.

11. The gas analyzer as claimed in claim 6, further comprising:
high-pass filters arranged upstream of the correlator, said high-pass filters high-pass filtering the measuring signal and the monitor signal (19) before correlation with a cut-off frequency having a level which is lower than a frequency level of the radio-frequency noise signal.

12. The gas analyzer as claimed in claim 11, wherein the evaluation device is configured to evaluate the correlation signal based on direct absorption spectroscopy.

13. The gas analyzer as claimed in claim 11, further comprising:
a low-frequency modulation device which controls the current source to additionally modulate the current with a lower amplitude and at least one additional frequency which is selected at a level which ensure wavelength modulation occurs;
wherein the evaluation device is configured to evaluate the correlation signal based on wavelength modulation spectroscopy.

14. The gas analyzer as claimed in claim 6, wherein the evaluation device is configured to evaluate the correlation signal based on direct absorption spectroscopy.

15. The gas analyzer as claimed in claim 14, further comprising:
a low-frequency modulation device which controls the current source to additionally modulate the current with a lower amplitude and at least one additional frequency which is selected at a level which ensure wavelength modulation occurs;
wherein the evaluation device is configured to evaluate the correlation signal based on wavelength modulation spectroscopy.

16. The gas analyzer as claimed in claim 6, further comprising:
a low-frequency modulation device which controls the current source to additionally modulate the current with a lower amplitude and at least one additional frequency which is selected at a level which ensure wavelength modulation occurs;
wherein the evaluation device is configured to evaluate the correlation signal based on wavelength modulation spectroscopy.

* * * * *